United States Patent [19]
Mori et al.

[11] 3,946,307
[45] Mar. 23, 1976

[54] APPARATUS FOR DETECTING THE PHYSICAL PROPERTIES OF MAGNETIC OR ELECTRIC CONDUCTIVE HEAT-RESPONSIVE OR DEFORMABLE MATERIAL USING NEGATIVE INPUT IMPEDANCE NETWORK

[75] Inventors: Toshiro Mori, Yokohama; Seigo Ando, Kawasaki, both of Japan

[73] Assignee: Nippon Kokan Kabushiki Kaisha, Tokyo, Japan

[22] Filed: Apr. 23, 1974

[21] Appl. No.: 463,254

[30] Foreign Application Priority Data
Apr. 25, 1973 Japan................................ 48-46950
June 30, 1973 Japan................................ 48-74156
Aug. 31, 1973 Japan................................ 48-97873

[52] U.S. Cl. .......... 324/34 R; 73/88 R; 73/362 AR; 324/40
[51] Int. Cl.² ........................................ G01R 33/12
[58] Field of Search ............ 324/34 R, 34 D, 34 PS, 324/37, 40, DIG. 1; 333/80 R, 80 T; 323/75 J, 75 K, 75 L, 75 M, 75 N, 75 S; 73/88.5 R, 362 AR

[56] References Cited
UNITED STATES PATENTS
3,461,400  8/1969  Koda...................................... 324/40
3,732,443  5/1973  Lovrenich....................... 324/DIG. 1

*Primary Examiner*—Robert J. Corcoran
*Attorney, Agent, or Firm*—Flynn & Frishauf

[57] ABSTRACT

A measuring apparatus uses an impedance element whose impedance varies with the physical properties of an object consisting of magnetic or electric conductive, heat-responsive or deformable substance, under the condition where the impedance element is energized by a D.C. or A.C. voltage source of a predetermined level. Connected in parallel or series with the impedance element is a negative impedance network, with its input impedance set at a negative value, which comprises an amplifier and positive and negative feedback impedance networks each connected between the input and output terminals of the amplifier. At least either of the positive and negative feedback impedance networks is constituted by a low, high or band pass filter for eliminating an external noise component, whereby the measuring apparatus enables to detect the physical properties of the object with as high a sensitivity and accuracy as possible.

18 Claims, 15 Drawing Figures

APPARATUS FOR DETECTING THE PHYSICAL PROPERTIES OF MAGNETIC OR ELECTRIC CONDUCTIVE HEAT-RESPONSIVE OR DEFORMABLE MATERIAL USING NEGATIVE INPUT IMPEDANCE NETWORK

This invention relates to an improvement on a measuring apparatus wherein any abnormal portion of an object of magnetic or electric conductive, heat-responsive or deformable material is detected by utilizing an impedance element whose impedance changes with the variation in the physical properties of the object.

Such a measuring apparatus includes one type which is designed to detect a voltage or the change thereof appearing across an inductance coil which is disposed with a small gap (generally 2 to 10 mm) to any portion of a sample consisting of magnetic or electric conductive material such as iron, steel, tin, copper or aluminum sheet and whose effective impedance changes with variations in the physical properties of the sample, under the conditions where the inductance coil is excited by a D.C. source of a predetermined voltage (generally 1 to 2 volts) or an A.C. source of a predetermined root mean square voltage and a frequency (generally 5 to 100 kHz).

It is assumed in the measuring apparatus constructed as described above that the sample is continuously transferred in a predetermined lengthwise direction.

If, under this condition, any physical defect such as pinholes, scratches, uneven thickness, concaves, convexes, adulteration by impurities, insufficiently welded portions, deformed portions or abnormal temperature occurs in that portion of the sample which faces the excited inductance coil, then the electric conductivity or magnetic permeability of the sample will vary at its defecting portion. Consequently, the quality of magnetic or eddy current which flows through the sample in accordance with the magnitude of the D.C. or A.C. magnetic field induced across the excited inductance coil will vary, causing the effective impedance of the excited inductance coil to be changed. As a result, detection of a voltage, or the change thereof, appearing across the inductance coil caused by variations in the effective impedance thereof can readily indicate those portions of the sample where the physical property thereof has changed. Such a measuring apparatus includes another type which is designed to detect a voltage or the change thereof appearing across a pair of main electrodes of a magnetoconductive semiconductor element such as a diode which is positioned with a small gap (generally 2 to 5 mm) to any portion of a sample consisting of magnetic material such as iron or steel sheet, under the condition where the magnetoconductive semiconductor element is energized by the aforesaid D.C. or A.C. source which is applied across the pair of main electrodes of the semiconductor element and the sample is previously magnetized. It is supposed in the measuring apparatus thus constructed that the magnetized sample is continuously moved in a predetermined lengthwise direction.

If, under this condition, any of the above-mentioned physical defects occurs in that portion of the sample which is opposed to the energized magnetoconductive semiconductor element, then the quality of leakage magnetic flux which is projected from the magnetized sample and interlinked with the magnetoconductive semiconductor element will vary at the defecting portion of the sample. Consequently the internal resistance of the magnetoconductive semiconductor element will vary, causing the voltage level which is induced across the pair of main electrodes thereof to be changed. Accordingly, it will be apparent that any physical defect in the magnetized sample can be easily detected by the measuring apparatus constructed as mentioned above, in the same manner as the measuring apparatus utilizing the aforesaid inductance coil.

Such a measuring apparatus further includes a temperature detection device adapted to detect a voltage or the change thereof appearing across a heat-responsive resistance element such as a thermistor disposed to directly contact with any portion of a sample consisting of heat-responsive material such as iron or steel sheet, under the condition where the heat-responsive resistance element is made conductive by the aforesaid D.C. or A.C. source which is applied thereacross.

Such a measuring apparatus also includes a strain-resistance gauge which is designed to detect a voltage or the change thereof appearing across a strain-resistance element attached to any portion of a sample consisting of deformable material such as rolled iron or steel sheet, under the condition where the strain-resistance element is rendered conductive by the aforesaid D.C. or A.C. source which is impressed thereon.

With the temperature detection device or the strain-resistance gauge constructed as above-mentioned, abnormal temperature or deformation occurs in those portions of any sample contacting the heat-responsive resistance element or fitted to the strain-resistance element, then the resistance value of the corresponding resistance element will vary, enabling the portions of the sample presenting an abnormal temperature or deformation to be easily detected.

The above-mentioned type prior art measuring apparatuses are designed to detect by amplification through a conventional amplifier the voltage or the change thereof appearing across the impedance element consisting of the above-mentioned inductance coil, magnetoconductive semiconductor element, heat-responsive resistance element or strain-resistance element.

However, the prior art measuring apparatus has the disadvantage of enhancing its sensitivity to a certain extent using a large number of amplifiers, because changes in the voltage appearing across the aforesaid impedance element generally have a considerably small value.

The customary practice for improving the sensitivity of the measuring apparatus utilizing the aforesaid inductance coil is to employ an A.C. source generating an input A.C. voltage of a predetermined frequency for exciting the inductance coil and to connect a capacitor in parallel or series with the inductance coil so as to form a resonance circuit which is tuned to the frequency of the input voltage source.

Although the conventional measuring apparatus provided with the resonance circuit has a higher sensitivity than any other apparatus not provided therewith, the former apparatus has the disadvantage of not only carrying out measurement merely at the resonance frequency of the resonance circuit, but also being more reduced in measuring accuracy due to fluctuation in the frequency of the input voltage as the sensitivity is enhanced.

Under such circumferences, the present inventors have recently developed an unbalance or balance type measuring apparatus which is designed to detect an abnormal physical defect in any of the above-mentioned sample with as high a sensitivity and accuracy as possible without being almost affected by the frequency of the input voltage, by utilizing a negative impedance network constructed as hereinunder described.

FIG. 1 shows a schematic circuit arrangement of the unbalance type measuring apparatus. In FIG. 1, reference numeral 11 denotes an input reference voltage source comprising a D.C. source of a predetermined voltage, for example, 1 to 2 volts or an A.C. source which generates an A.C. voltage having a predetermined root mean square value, e.g. 1 to 2 volts and a given frequency ranging from 5 to 100 kHz. Connected across the input reference voltage source 11 via an impedance element 12 for impedance matching is an impedance element 13 comprising an inductance coil, a magnetoconductive semiconductor element, a heat-responsive resistance element or a strain-resistance element which is disposed in the manner as described above to any of the aforesaid samples. Thus, connected in parallel (or series) with the impedance element 13 is a negative impedance network 16, with its input impedance set at a negative value as later described, which comprises a conventional amplifier 14 and a positive feedback impedance element 15 connected between the input and output terminals of the amplifier 14.

As seen from the side of the input terminals I1 and I2 of the impedance element 13 where the output terminals O1 and O2 of the negative impedance network 16 are open-circuited, the input impedance Zin of the circuit of FIG. 1 used as the measuring apparatus thus constructed is expressed as follows:

$$Zin = \frac{Z1 \times Zi}{Z1 + Zi} \quad (1)$$

where

Z1: the impedance of the impedance element 13
Zi: the input impedance of the negative impedance network 16

Designating the amplification factor of the amplifier 14 as A and the impedance of the positive feedback impedance element 15 as Z2, the input impedance Zi of the negative impedance network 16 is expressed by the following equation:

$$Zi = \frac{Z2}{1 - A} \quad (2)$$

Substituting equation (2) in equation (1), we obtain $$Zin = \frac{\frac{Z1 \cdot Z2}{1 - A}}{Z1 + \frac{Z2}{1 - A}} = \frac{Z1}{1 - \frac{Z1}{Z2}} \quad (3)$$

As apparent from equation (3), the input impedance Zin, with the output terminals O1 and O2 open-circuited, varies from the impedance Z1 of the impedance element 13 to infinity and further to a negative value depending upon the impedances Z1 and Z2 of the impedance element 13 and positive feedback impedance element 15 and the amplification factor A of the amplifier 14. Accordingly, the input terminals I1 and I2 of the impedance element 13 should be apparently open-circuited by previously selecting the values of the aforesaid impedances Z1 and Z2 and the aforesaid amplification factor A so that the input impedance Zin, with the output terminals O1 and O2 open-circuited, can have as high a value as possible, preferably an infinite value, thereby substantially to prevent the flow of any current from the input reference voltage source 11 to the impedance element 13. For this reason, the circuit shown in FIG. 1 acts as a circuit equivalent to a conventional parallel resonance circuit without being tuned to the frequency of an input signal from the input reference voltage source 11 and has the advantage of detecting a voltage representing the aforesaid abnormal portions of any of the above-mentioned samples in the considerably enlarged form or the change of said voltage appearing across the impedance element 13, without being affected by fluctuation in the frequency of the input signal.

In this case, a circuit portion 16 including the amplifier 14 and the positive feedback impedance element 15 must constitute a negative impedance network, with its input impedance set at a negative value, so that the amplifier 14 can have its amplification factor A chosen to have a larger value than at least 1, as apparent from equations (2) and (3).

Moreover, the circuit of FIG. 1 can operate very stably if a relatively high amplification factor is selected for the amplifier 14 and a negative feedback loop is further provided in the negative impedance network 16.

FIG. 2 shows a schematic circuit arrangement of a balance type measuring apparatus constructed in accordance with the same operational principle as the circuit of FIG. 1. Connected across an input reference voltage source 21 constituted in the same manner as the input reference voltage source 11 of FIG. 1 are the input terminals I11 and I12 of a bridge circuit 26 comprising an impedance element 22 similar to the impedance element 13 disposed in the above-described manner to any of the aforesaid samples and three other impedance elements 23, 24 and 25. Thus, connected to the output terminals O11 and O12 of the bridge circuit 26 are a pair of negative impedance networks 291 and 292 each having the same construction as the negative impedance network 16 shown in FIG. 1 and each comprising a conventional amplifier 271 or 272 and a positive feedback impedance element 281 or 282 connected between the input and output terminals of the corresponding amplifier 271 or 272.

It is well known to those skilled in the art that, where the impedances of the respective impedance elements 22 to 25 jointly constituting the bridge circuit 26 are previously adjusted to prevent any output signal from being produced across the output terminals O11 and O12 of the bridge circuit 26 under the condition where the impedance element 22 takes a position related to that portion of the sample which exhibits a standard physical property free from any of the aforesaid defects, the measuring apparatus thus constructed acts to deliver from the output terminals of the bridge circuit 26 an electric signal representing those portions of the sample which exhibit the above-mentioned abnormal physical properties only when the impedance element 22 takes a position related to the abnormal portions of the sample. The electric signal thus obtained is remarkably enlarged by the pair of negative impedance networks 291 and 292, enabling those portions of the sample which exhibit any abnormal physical property to be detected with a high sensitivity.

However, the measuring apparatus constructed as shown in FIG. 2 has the disadvantage that not only its circuit composition is relatively complicated because of requiring two amplifiers but also its measuring accuracy is relatively low because these amplifiers generally have different electric characteristics.

Furthermore, if the unbalance type measuring apparatus of FIG. 1 as well as the balance type measuring apparatus of FIG. 2 is used under the circumference where an external noise signal of any frequency exists, then it has the shortcoming of detecting with a high sensitivity the external noise signal component in addition to the desired signal component representing the aforesaid abnormal portions of any sample.

It is, therefore, the object of this invention to provide a measuring apparatus capable of detecting with as high a sensitivity and accuracy as possible those portions of a sample consisting of magnetic or electric conductive, heat-responsive or deformable material which bear the above-mentioned abnormal physical properties without being affected by at least the frequency of an input signal from a measuring input signal source.

SUMMARY OF THE INVENTION

The measuring apparatus according to the preferred embodiment of this invention is characterized in that there is provided a negative impedance network, with its input impedance set at a negative value, comprising a differential type operational amplifier having input terminals connected to the output terminals of a bridge circuit whose input terminals are connected across an input D.C. or A.C. reference voltage source of a predetermined voltage and which comprises an impedance element disposed close to, or in direct contact with, a sample of electric or magnetic conductive heat-responsive, or deformable material and at least three other impedance elements and having an impedance varied with the physical properties of the sample; and at least positive feedback impedance network connected between the input and output terminals of the operational amplifier.

The measuring apparatus thus constructed has the advantage of detecting with a high sensitivity and accuracy by a relatively simple circuit construction those portions of the sample which exhibit the above-mentioned abnormal physical properties without being affected by the frequency of an input voltage from the reference voltage source.

The measuring apparatus according to another embodiment of this invention is provided with a negative impedance network, with its input impedance set at a negative value, comprising an amplifier connected in parallel or series with an impedance element which is connected to an input D.C. or A.C. reference voltage source of a predetermined voltage, which is disposed close to, or in direct contact with, a sample of electric or magnetic conductive, heat-responsive or deformable material, and whose impedance is varied with the physical properties of the sample; and positive and negative feedback impedance networks connected between the input and output terminals of the amplifier, and the measuring apparatus is characterized in that at least either of the positive and negative feedback networks included in the negative impedance network comprises a filter circuit acting to feed only a predetermined frequency component with a lower or higher level than the remaining frequency components from the input side of the amplifier back to the output side thereof.

The measuring apparatus thus constructed has the advantage of detecting with as high a sensitivity and accuracy as possible those portions of the sample which bear the aforesaid abnormal physical properties, without being affected by the frequency of an input voltage from the reference voltage source as well as any external noise signal component.

BRIEF DESCRIPTION OF THE DRAWINGS

This invention can be more fully understood from the following detailed description when taken in conjunction with the accompanying drawings, in which.

DETAILED DESCRIPTION OF ILLUSTRATED EMBODIMENT

Figure 3:
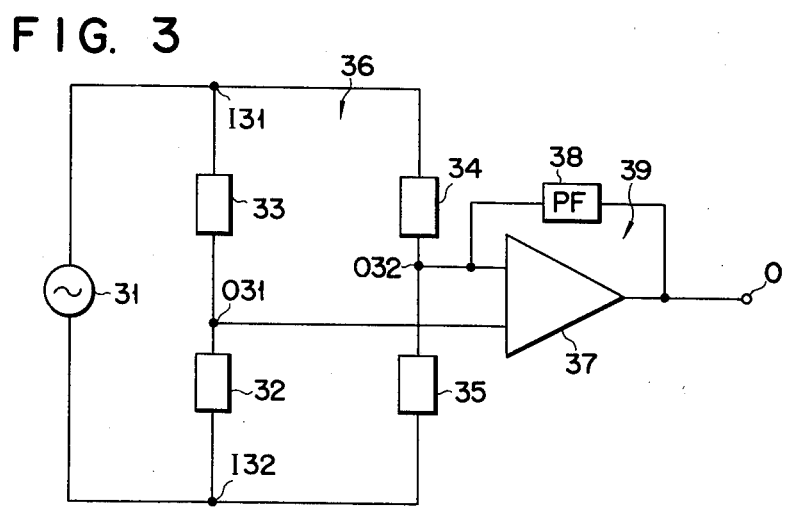
FIG. 3 shows a schematic circuit diagram of a measuring apparatus according to one embodiment of this invention.

FIG. 3 shows a schematic circuit diagram of a measuring apparatus according to one embodiment of this invention. In FIG. 3, reference numeral 31 denotes an input reference voltage source constituted by a D.C. source which generates a D.C. voltage of a predetermined value, e.g. about 1 to 2 volts or an A.C. source which generates an A.C. voltage having a predetermined value, e.g. about 1 to 2 peak-to-peak voltage and a predetermined frequency (any frequency of about 5 to 100 kHz). Connected across the input reference voltage source 31 are the input terminals I31 and I32 of a bridge circuit 36 which is constituted by four impedance elements 32, 33, 34 and 35 each comprising an inductance or any type resistance element.

Figure 4A:
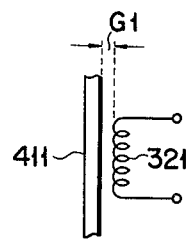
FIGS. 4A to 4D are schematic diagrams illustrating different compositions of the impedance element 32 shown in FIG. 3.
Figure 4B:
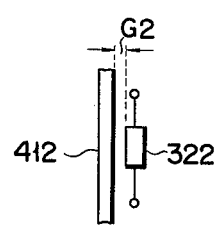
Figure 4C:
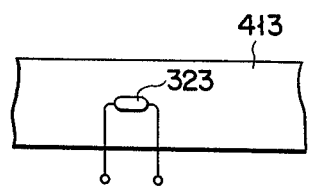
Figure 4D:
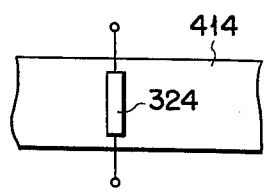

At least one, for example, 32 of the four impedance elements 32 to 35 comprises an inductance coil 321 disposed with a small gap G1 of about 2 to 10 mm to any portion of a sample 411 consisting of magnetic or electric conductive material such as iron, steel, copper or aluminum sheet, as shown in FIG. 4A; a magnetoconductive semiconductor element 322 disposed with a small gap G2 of about 2 to 5 mm to any portion of a sample 412 consisting of magnetic material such as iron or steel sheet, as shown in FIG. 4B; a heat-responsive resistance element 323 such as a thermistor directly contacting any portion of a sample 413 consisting of heat-responsive material such as any metal, as shown in FIG. 4C; or a strain-resistance element 324 fitted to any portion of a sample 414 consisting of deformable material such as rolled steel or iron sheet, as shown in FIG. 4D.

The other three impedance elements 33 to 35 constituting the bridge circuit 36 may each comprise an inductance coil where the impedance element 32 is the inductance coil 321 as shown in FIG. 4A; a magnetoconductive semiconductor element or a conventional resistor where the impedance element 32 is the magnetoconductive semiconductor element 322 as shown in FIG. 4B; a heat-responsive resistance element or a conventional resistor where the impedance element 32 is the heat-responsive resistance element 323 as shown in FIG. 4C; or a conventional resistor where the impedance element 32 is the strain-resistance element 324 as shown in FIG. 4D.

Referring to again to FIG. 3, a negative impedance network 39 constructed as hereinunder described is provided. The negative impedance network 39 comprises a differential type operational amplifier 37 whose input terminals are connected to the output terminals O31 and O32 of the bridge circuit 36, and a positive feedback impedance network 38 connected to one input terminal and the output terminal O of the operational amplifier 37, the negative impedance network 39 being constructed to have a negative input impedance by previously making the amplification factor of the operational amplifier 37 a larger value than 1.

The operation of the circuit of FIG. 3 will be described. Where the bridge circuit 36 is previously constructed to prevent any output signal from being delivered across the output terminals O31 and O32 thereof under the condition the impedance element 32 takes a position related to that portion of the sample 411, 412, 413 or 414 (see FIGS. 4A to 4D) which exhibits a standard physical property free from any of the above-mentioned defects, then the circuit of FIG. 3 acts to produce from the output terminals O31 and O32 of the bridge circuit 36 an electric signal representing those portions of the sample which bear the above-mentioned abnormal physical properties only when the impedance element 32 takes a position related to the abnormal portions of the sample. The electric signal thus obtained is remarkably enlarged by the negative impedance network 39, whereby the circuit of FIG. 3 can detect with a high sensitivity any abnormal portion of the sample.

Figure 1:
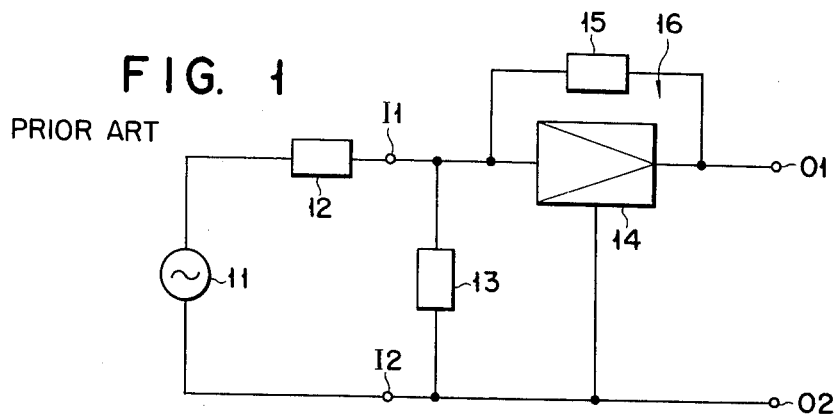
FIG. 1 shows a schematic circuit diagram of a prior art unbalance type measuring apparatus recently developed by the present inventors.
Figure 2:
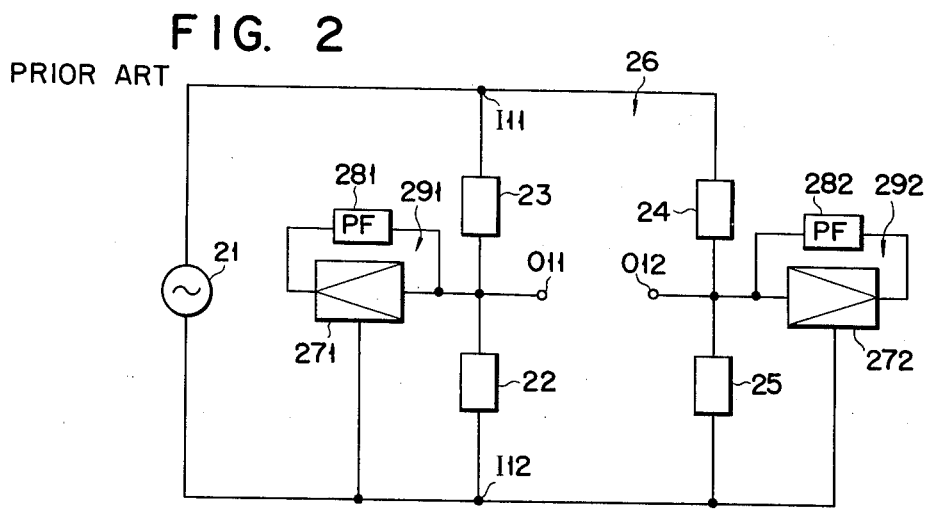
FIG. 2 shows a schematic circuit diagram of a prior art balance type measuring apparatus recently developed by the inventors.

The measuring apparatus constructed as shown in FIG. 3 has the advantage of detecting any abnormal portion of the sample with a higher accuracy than the measuring apparatus of FIG. 2 utilizing a simpler circuit arrangement than that of FIG. 2, because the single negative impedance network 39 utilizing the operational amplifier 37 is replaced by the two negative impedance networks 291 and 292 employing the two conventional amplifiers 271 and 272 whose electric characteristics are generally different.

In the case where the impedance element 32 used in the measuring apparatus is the magnetoconductive semiconductor element 322 as shown in FIG. 4B, the measuring apparatus has a tendency of carrying out an erroneous detection since a magnetoconductive semiconductor element generally has an internal resistance varied with temperature.

Figure 5:
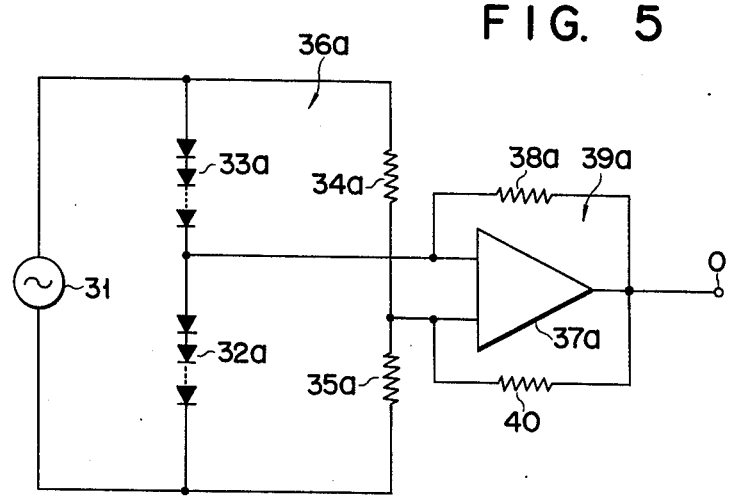
FIG. 5 shows a practical circuit arrangement of a measuring apparatus modified from the embodiment of FIG. 3 where the impedance element 32 of FIG. 3 is a magnetoconductive semiconductor diode disposed close to a sample consisting of magnetic material whose magnetic characteristic is to be detected.

FIG. 5 shows a practical circuit arrangement of a measuring apparatus modified from the embodiment of FIG. 3 suitable for reducing the possibility of the erroneous detection.

In the measuring apparatus of FIG. 5, the impedance element 32 used in the bridge circuit 36 of FIG. 3 is replaced by a plurality of series-connected magnetoconductive diodes 32a; the impedance element 33 of FIG. 3 by a plurality of series-connected magnetoconductive diodes 33a disposed close to the sample 412 as shown in FIG. 4B being measured in the same manner as the diodes 32a; and the impedance elements 34 and 35 of FIG. 3, by conventional resistors 34a and 35a. Connected across the output terminals of a bridge circuit 36 constituted by said diodes 32a and 33a and resistors 34a and 35a is a negative impedance network 39a comprising a differential type operational amplifier 37a, and positive and negative feedback resistors 38a and 40 connected between one input and output terminals of the bridge circuit 36a.

It will be apparent to those skilled in the art that the measuring apparatus thus constructed can considerably reduce the possibility of an erroneous detection due to the temperature variation of the individual magnetoconductive diodes used for the measurement.

Figure 6:
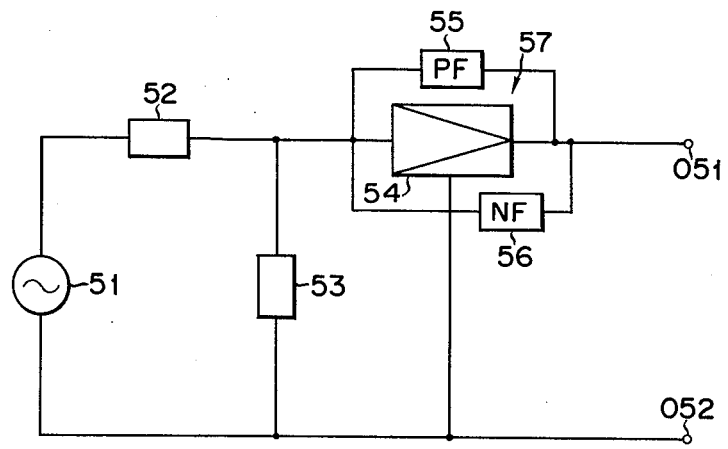
FIG. 6 shows a schematic circuit diagram of an unbalance type measuring apparatus according to another embodiment of this invention.

FIG. 6 shows a schematic circuit diagram of a measuring apparatus according to another embodiment of this invention.

In FIG. 6, reference numeral 51 denotes an input reference voltage source having the same construction as that FIG. 3.

An impedance element 53 the same as the impedance element 32 of FIG. 3 is connected across the input reference voltage source 51 via an impedance element 52 for impedance-matching. Connected in parallel (or series) with the impedance element 53 is a negative impedance network 57 comprising an amplifier 54, and positive and negative feedback impedance networks 55 and 56.

Thus, at least either of the positive and negative feedback impedance networks 55 and 56 included in the negative impedance network 57 comprises a filter circuit constructed as hereinunder described to eliminate any external noise signal component.

Figure 7A:
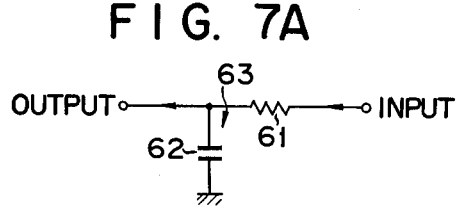
FIGS. 7A to 7D are practical circuit arrangements of different filter circuits each constituting the positive and/or negative impedance network included in the negative impedance network shown in FIG. 6.
Figure 7B:
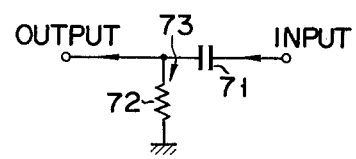

FIG. 7A shows one example of the filter circuit used as the positive feedback impedance network 55 and/or the negative feedback impedance network 56. The filter circuit comprises a low pass filter 63 constituted by an integral circuit including a resistor 61 and a capacitor 62. FIG. 7B shows another example of the aforesaid filter circuit used in the circuit of FIG. 6. The filter circuit comprises a high pass filter 73 constructed of a differentiation circuit including a capacitor 71 and a resistor 72.

Figure 7C:
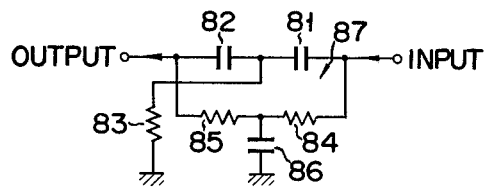
Figure 7D:
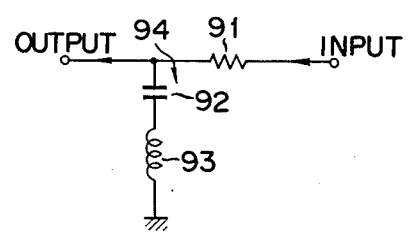

FIG. 7C shows a further example of the aforesaid filter circuit employed in the circuit of FIG. 6. The filter circuit comprises a band pass filter 87 constituted by a twin-T circuit which includes two series-connected capacitors 81 and 82, two series-connected resistors 84 and 85 connected in parallel with the series-connected capacitors 81 and 82, a resistor 83 connected between ground and the common junction of the capacitors 81 and 82, and a capacitor connected between the ground and the common junction of the resistors 84 and 85. FIG. 7D shows a still another example of the aforesaid filter circuit used in the circuit of FIG. 6.

The filter circuit comprises a band pass filter 94 constituted by a series (or parallel) resonance circuit including a resistor 91 provided if necessary, a capacitor 92 and an inductance coil 93.

If the low pass filter 63 constructed as shown in FIG. 7A, the high pass filter 73 constituted as shown in FIG. 7B, or the band pass filter 87 or 94 constructed as shown in FIG. 7C or 7D is used for the positive feedback impedance network 55 and/or the negative feedback impedance network 56 shown in FIG. 6, then the measuring apparatus can easily eliminate an external noise signal component having any frequency, thereby enabling only the desired signal component representing any of the above-mentioned abnormal portions of the sample being measured to be delivered in the enlarged form either across both the terminals of the impedance element 53 or the output terminals O51 and O52 of the negative impedance network 57. Both outputs provide similar effects.

For example, the present inventors, experiments show that it is preferable to employ the low pass filter having its cutoff frequency of about 0.01 to 10 Hz for the negative feedback impedance network 56 included in the negative impedance network 57 shown in FIG. 6.

Figure 8:
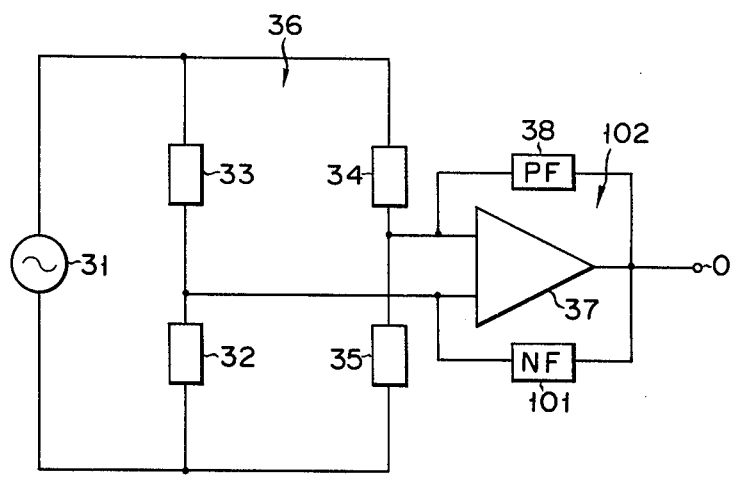
FIG. 8 shows a schematic circuit diagram of a balance type measuring apparatus according to a still another embodiment of this invention.

FIG. 8 shows a schematic circuit diagram of a balance type measuring apparatus according to a further embodiment of this invention.

This embodiment is the same circuit composition as the embodiment of FIG. 3, except that a negative impedance network 102 connected across the output terminals of the bridge circuit 36 is further provided with a negative feedback impedance network 101 connected between one input and output terminals of the operational amplifier 37 in addition to the positive feedback impedance network 38; and at least either of the positive and/or negative feedback impedance network is constituted by any of the low, high and band pass filters shown in FIGS. 7A to 7D.

It will be apparent that the measuring apparatus thus constructed acts in substantially the same manner as that of FIG. 6.

Figure 9:
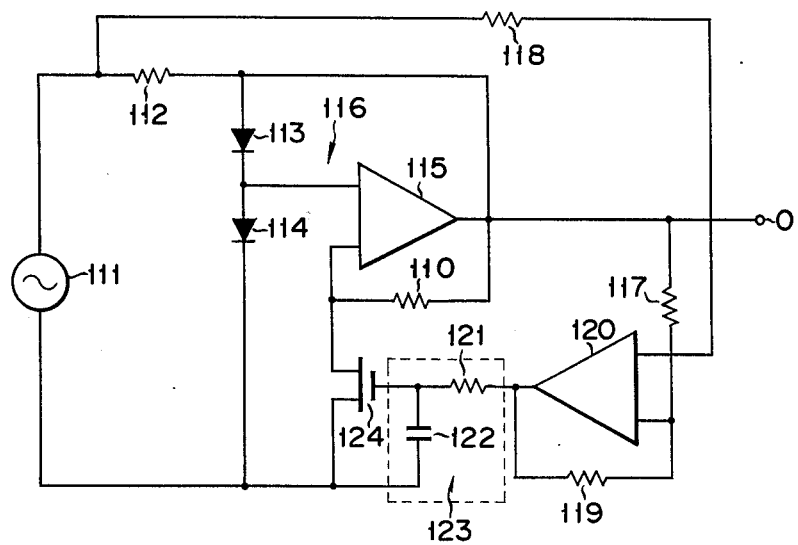
FIG. 9 shows a practical circuit arrangement of a measuring apparatus in accordance with this invention suitable for detecting the magnetic properties of any magnetic material utilizing a magnetoconductive semiconductor diode.

FIG. 9 shows a practical circuit arrangement of a measuring apparatus embodying this invention.

In FIG. 9, reference numeral 111 denotes an input reference voltage source having the same construction as the input reference voltage source 31 shown in FIG. 3. Connected in series across the input reference voltage source 111 are two magnetoconductive diodes 113 and 114 via a resistor 112. Either of the diodes is disposed with a small gap to any portion of a sample consisting of any magnetic material to be measured, while the other diode is provided with the same gap as the first-mentioned diode to that portion of the sample which bears a standard physical property free from the aforesaid abnormal defects.

A negative impedance network 116 constructed as hereinunder described is provided with respect to the magnetoconductive diodes 113 and 114. The negative impedance network 116 comprises a differential type operational amplifier 115 having one input terminal connected to the output terminal O thereof via the diode 113 concurrently acting as a positive feedback resistance element and the other input terminal connected to the output terminal O of the amplifier 115 via a negative feedback resistor 110 and also to one terminal of the input reference voltage source 111 via the drain-source path of a field effect transistor 124; another differential type operational amplifier 120 one input terminal of which is connected via a resistor 118 to the other terminal of the input reference voltage source 111 and the other input terminal of which is connected to the output terminal thereof via a resistor 119 and also to the output terminal O of the first-mentioned operational amplifier 115 via a resistor 117; and a low pass filter 123 constituted by an integral circuit including a resistor 121 and a capacitor 122, having an input terminal connected to the output terminal of the second-mentioned operational amplifier 120 and having an output terminal connected to the gate electrode of the field effect transistor 124. The second-mentioned operational amplifier 120, the low pass filter 123, the field effect transistor 124 and the resistor 110 jointly constitute a negative feedback network for the negative impedance network 116.

The measuring apparatus thus constructed has the advantage of detecting with a higher accuracy than that of FIG. 5 any of the aforesaid abnormal defecting portions of the sample being measured utilizing the single magnetoconductive diodes 113 and 114 for the plurality of series-connected magnetoconductive diodes 32a and 33a used in the measuring apparatus of FIG. 5, by previously selecting the cutoff frequency of the low pass filter 123 to an appropriate value.

It should be understood that the invention is by no means limited to the particular embodiments illustrated but that many changes and modifications may be permissible without departing the scope of the invention.

What we claim is:

1. A measuring apparatus for measuring physical properties of a sample, comprising:

a pair of terminals supplying an input reference voltage of a predetermined value;

a bridge circuit whose input terminals are connected to said pair of terminals, said bridge circuit comprising: a variable impedance element disposed adjacent a sample of magnetic or electric conductive, heat-responsive or deformable material and having an impedance which varies with the physical properties of the sample being measured; and at least three other impedance elements coupled with said variable impedance element in a bridge arrangement;

a negative impedance network including: a differential type operational amplifier having a negative value of input impedance and having its input terminals coupled to the output terminals of said bridge circuit; and at least one positive feedback impedance network coupled between the input and output terminals of said differential type operational amplifier; and means for deriving an output signal corresponding to the signal appearing at at least one terminal of said differential type operational amplifier, said output signal varying as a function of a change in balance of said bridge responsive to a change in physical properties of said sample being measured.

2. A measuring apparatus according to claim 1 wherein said input reference voltage is a D.C. voltage of a predetermined value.

3. A measuring apparatus according to claim 1 wherein said input reference voltage is an A.C. voltage of a predetermined value.

4. A measuring apparatus according to claim 1 wherein said variable impedance element of said bridge circuit is disposed close to said sample being measured.

5. A measuring apparatus according to claim 1 wherein said variable impedance element of said bridge circuit is disposed in contact with said sample being measured.

6. A measuring apparatus for measuring physical properties of a sample, comprising:
an input reference voltage source supplying an input reference voltage of a predetermined value;
a first impedance element coupled to said input reference voltage source;
a variable impedance element coupled to said input reference voltage source via said first impedance element, said variable impedance element being disposed adjacent a sample of magnetic or electric conductive, heat-responsive or deformable material and having an impedance which varies with the physical properties of the sample being measured;
a negative impedance network including: an amplifier coupled to said variable impedance element; a positive feedback impedance circuit coupled between the input and output terminals of said amplifier; and a negative feedback impedance circuit coupled between the input and output terminals of said amplifier;
at least one of said positive and negative feedback impedance circuits included in said negative impedance network comprising a filter circuit feeding from the output side of said amplifier back to the input side of said amplifier only signal components representing those portions of the sample which exhibit abnormal physical properties, said signal components representing said abnormal physical properties having a different level than other signal components; and
means for deriving an output signal corresponding to the signal appearing at at least one terminal of said amplifier, said output signal varying as a function of said signal components representing said abnormal physical properties which are generated responsive to the presence of abnormal physical properties of said sample being measured.

7. A measuring apparatus claimed in claim 6 wherein said filter circuit comprises a low pass filter 8. A measuring apparatus claimed in claim 6 wherein said filter circuit comprises a high pass filter.

9. A measuring apparatus claimed in claim 6 wherein said filter circuit comprises a band pass filter.

10. A measuring apparatus according to claim 6 wherein both said positive and negative feedback impedance circuits comprise a filter circuit.

11. A measuring apparatus according to claim 6 wherein said input reference voltage source supplies a D.C. input reference voltage of predetermined value.

12. A measuring apparatus according to claim 6 wherein said input reference voltage source supplies an A.C. input reference voltage of predetermined value.

13. A measuring apparatus according to claim 6 wherein said variable impedance element is disposed close to said sample being measured.

14. A measuring apparatus according to claim 6 wherein said variable impedance element is disposed in contact with said sample being measured.

15. A measuring apparatus according to claim 6 wherein said amplifier is coupled in parallel with said variable impedance element.

16. A measuring apparatus according to claim 6 wherein said amplifier is coupled in series with said variable impedance element.

17. A measuring apparatus according to claim 6 wherein said variable impedance element is coupled to an input terminal of said amplifier.

18. A measuring apparatus according to claim 6 wherein said amplifier is an operational amplifier.

* * * * *